United States Patent
Dumoulin et al.

[19]

[11] Patent Number: 6,129,667
[45] Date of Patent: *Oct. 10, 2000

[54] LUMINAL DIAGNOSTICS EMPLOYING SPECTRAL ANALYSIS

[75] Inventors: Charles Lucian Dumoulin, Ballston Lake; Robert David Darrow, Scotia; Ronald Dean Watkins, Niskayuna, all of N.Y.

[73] Assignee: General Electric Company, Schenectady, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/017,565

[22] Filed: Feb. 2, 1998

[51] Int. Cl.⁷ ....................................................... A61B 5/00
[52] U.S. Cl. ........................................... 600/424; 600/477
[58] Field of Search ....................................... 600/473, 475, 600/476, 477, 478, 424, 342, 343, 310, 410, 420, 407, 137, 117, 160, 182; 356/345, 346

[56] References Cited

U.S. PATENT DOCUMENTS

| | | |
|---|---|---|
| 5,010,886 | 4/1991 | Passafaro et al. . |
| 5,307,808 | 5/1994 | Dumoulin et al. . |
| 5,377,678 | 1/1995 | Dumoulin et al. . |
| 5,408,998 | 4/1995 | Mersch . |
| 5,441,053 | 8/1995 | Lodder et al. . |
| 5,582,171 | 12/1996 | Chornenky et al. . |
| 5,678,550 | 10/1997 | Bassen et al. . |
| 5,740,808 | 4/1998 | Panescu et al. . |
| 5,749,835 | 5/1998 | Glantz . |
| 5,752,518 | 5/1998 | McGee et al. . |
| 5,785,658 | 7/1998 | Benaron et al. . |
| 5,792,053 | 8/1998 | Skladnev et al. . |
| 5,823,942 | 10/1998 | Toida . |
| 5,827,190 | 10/1998 | Palcic et al. . |
| 5,840,035 | 11/1998 | Heusmann et al. ...................... 600/477 |
| 5,842,995 | 12/1998 | Mahadevan-Jansen et al. . |
| 5,851,181 | 12/1998 | Talmor . |
| 5,868,674 | 2/1999 | Glowinski et al. . |
| 5,899,860 | 5/1999 | Pfeiffer et al. .......................... 600/424 |
| 5,921,926 | 7/1999 | Rolland et al. . |
| 5,938,602 | 8/1999 | Lloyd ...................................... 600/424 |
| 5,951,482 | 9/1999 | Winston et al. . |
| 5,999,844 | 12/1999 | Gombrich et al. ....................... 600/476 |
| 6,006,128 | 12/1999 | Izatt et al. ............................... 600/476 |
| 6,016,439 | 1/2000 | Acker ...................................... 600/411 |
| 6,052,610 | 4/2000 | Koch ....................................... 600/424 |

*Primary Examiner*—Marvin M. Lateef
*Assistant Examiner*—Shawna J Shaw
*Attorney, Agent, or Firm*—Jean K. Testa; Donald S. Ingraham

[57] ABSTRACT

An invasive probe for determining the morphological characteristics of walls of a lumen employs a real-time tracking means and an optical spectral measurement means. As the probe is advanced within the lumen, the real-time tracking means provides three-dimensional coordinates of the probe's position and orientation. Concurrent with probe localization, measurement of the spectral properties of the lumen wall are made by detecting the reflectance and/or absorption of light at the lumen wall. Both the probe position and the spectral measurement are sent to a data acquisition system which in turn provides an graphic or numeric display to the operator. Probe tracking can be performed with radio-frequency, magnetic resonance, ultrasonic techniques or the like. If desired, spectral measurements can be made in the visible, ultra-violet or infra-red spectral bands to provide optimized detection of chemical species of interest.

8 Claims, 3 Drawing Sheets

LUMINAL DIAGNOSTICS EMPLOYING SPECTRAL ANALYSIS

BACKGROUND OF THE INVENTION

1. Field of the Invention

This invention relates to medical diagnostic systems to provide diagnostic image maps of lumens within the body.

2. Discussion of Prior Art

It is desirable to acquire an indication of the inside of lumens of a body of a subject to diagnose different medical dysfunctions.

X-ray methods bombard the subject with ionizing radiation, and may require addition of contrast agents which are uncomfortable to the subject. While X-ray methods can show blockage, they do not differentiate between different types of tissue which may be blocking the lumen.

Magnetic Resonance methods can differentiate between tissue types better than X-ray, but are relatively slow and expensive. Perhaps the most useful method for tissue differentiation is a visual examination. Unfortunately, this typically requires the surgical removal of tissue for diagnosis.

Currently there is a need for a method of examining the inside of lumens of a subject which provides visible coloration information without surgical excision.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

SUMMARY OF THE INVENTION

Figure 1:
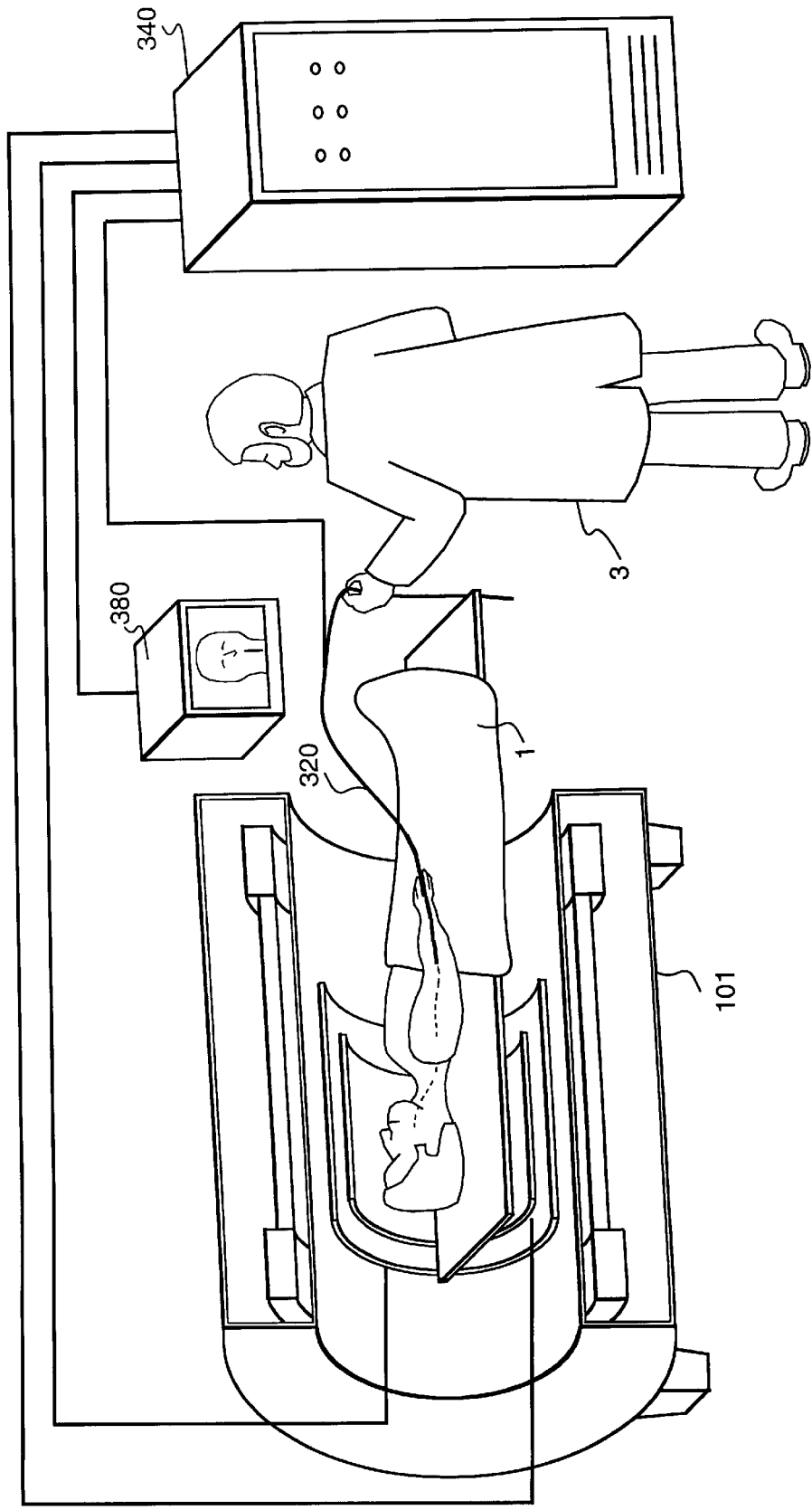
FIG. 1 is a simplified block diagram of the present invention employing an MR tracking system used to follow an invasive device in real-time.

A system for creating 3D tissue maps of a selected lumen within a subject employs an optical spectrum acquisition device in an insertion end of the invasive device, inserted into a lumen of the subject.

The optical spectrum acquisition device operates to create a light beam and directs it to intersect the lumen at several angular displacement θ around the invasive device. The outgoing light beam O is reflected from the lumen wall as a reflected light beam R having a spectrum characteristic of the tissue type at that location of the lumen at the reflection point.

A device locating means is attached to the insertion end of the invasive devce and is tracked by a tracking means, preferably in real time, which passes the location of the device locating means to a look up device.

A rotation sensor measures the angular displacement θ of the irradiating beam and also passes this to look up device 365. It is beneficial to rotate the outgoing beam O to acquire radial measurements before the invasive device moves significantly.

Look up device 365 converts the tracked location of the device locating means 261, and the angular displacement of the irradiating beam to estimate a 3D location of the lumen reflecting the irradiating beam. The look up device also correlates the reflected light spectrum with a known, stored tissue type.

The 3D location and the tissue type are stored in a storage device for later retrieval.

The look up device can also be operated to display the 3D locations and corresponding tissue type as a tissue map on a display according to operator defined input.

A user interface may be incorporated which is operated to receive operator defined input from the operator and provide this input to the lookup device.

In an alternative embodiment, an interferometer device may be connected to the fiber optic cable to receive the reflected light. It will then determine a distance D from the lumen to the optical spectrum acquisition device, thereby allowing accurate measurements of radii and diameter of the lumen at various locations. When this information is provided to the look up device, the 3D location on the lumen reflecting the irradiating beam may be determined, resulting in tissue maps incorporating actual measured lumen diameters. This results in actual 3D maps with tissue types superimposed upon it.

OBJECTS OF THE INVENTION

It is an object of the present invention to provide a diagnostic luminal map of the visual characteristics of a lumen wall of a subject.

It is another object of the present invention to provide a luminal map of tissue types from the visual light reflected from an internal lumen wall of a subject.

DETAILED DESCRIPTION OF THE INVENTION

Typically, vascular disease progresses in a somewhat predictable (although usually hidden) manner. Healthy arteries, such as those found in a newborn baby have three well defined layers: the endothelium, media and adventitia. The endothelium is located on the inner surface of the vessel, the media forms the internal structure of the vessel wall and the adventitia defines the outer wall. The endothelium is formed by a porous layer of tissue which is sensitive to the blood moving in the vessel. The adventitia is formed of fibrous material and has the ability to stretch somewhat.

The first step in the progression of arterial disease is the deposition of fatty material in the media layer of the vessel wall. Frequently the location of these deposits is associated with regions of low shear stress associated with vessel bifurcations. These deposits slowly increase in size and cause a thickening of the vessel wall. Because of the pressure of the arterial blood, however, the initial thickening of the wall does not result in a constriction of the internal lumen of the vessel. Rather, the adventitia is stretched and the internal lumen is maintained. At some point in the progression of the disease, however, the adventitia is stretched to its limit and further expansion is impossible. When this occurs, further increases in wall thickening result in a decrease in the caliber of the internal lumen. As the lumen caliber decreases, the local blood velocity increases and damage to the endothelial layer begins to occur. The simultaneous occurrence of a damaged endothelial layer, increased blood velocity and altered flow patterns due to a reduced internal lumen can result in the creation of ulcerations in the vessel wall. If these ulcers become large enough, they can create regions of slow or stagnant flow. Consequently, blood clots can form within the ulcers. Blood clots are not stable, however, and it is possible for portions to break away and become lodged downstream in the vascular system, causing a stroke or heart attack.

There are several variations to the typical progression of arterial disease. For example, if the disease progresses slowly enough, some of the fatty material deposited as a plaque in the wall of the vessel can be converted to a calcified material. Unlike fatty tissue, a calcified plaque is hard and brittle. It is also possible for a plaque to develop its own blood supply, with the formation of microscopic vasculature within the wall of the vessel.

Identification of plaques and differentiation among the types of plaques plays an important role in the diagnosis and treatment of vascular disease. Because they are relatively soft, fatty plaques tend to respond better to mechanical treatment such as balloon angioplasty than brittle calcified plaques. Hemorrhagic plaques, however, respond better to surgical interventions.

Optical spectroscopy has the potential to differentiate the different types of plaques and provide useful diagnostic information. Healthy arterial walls have a smooth pink appearance. Fatty plaques, on the other hand, appear somewhat bumpy and have a yellowish hue. Calcified plaques appear white while hemorrhagic plaques appear red or brownish-red.

Figure 2:
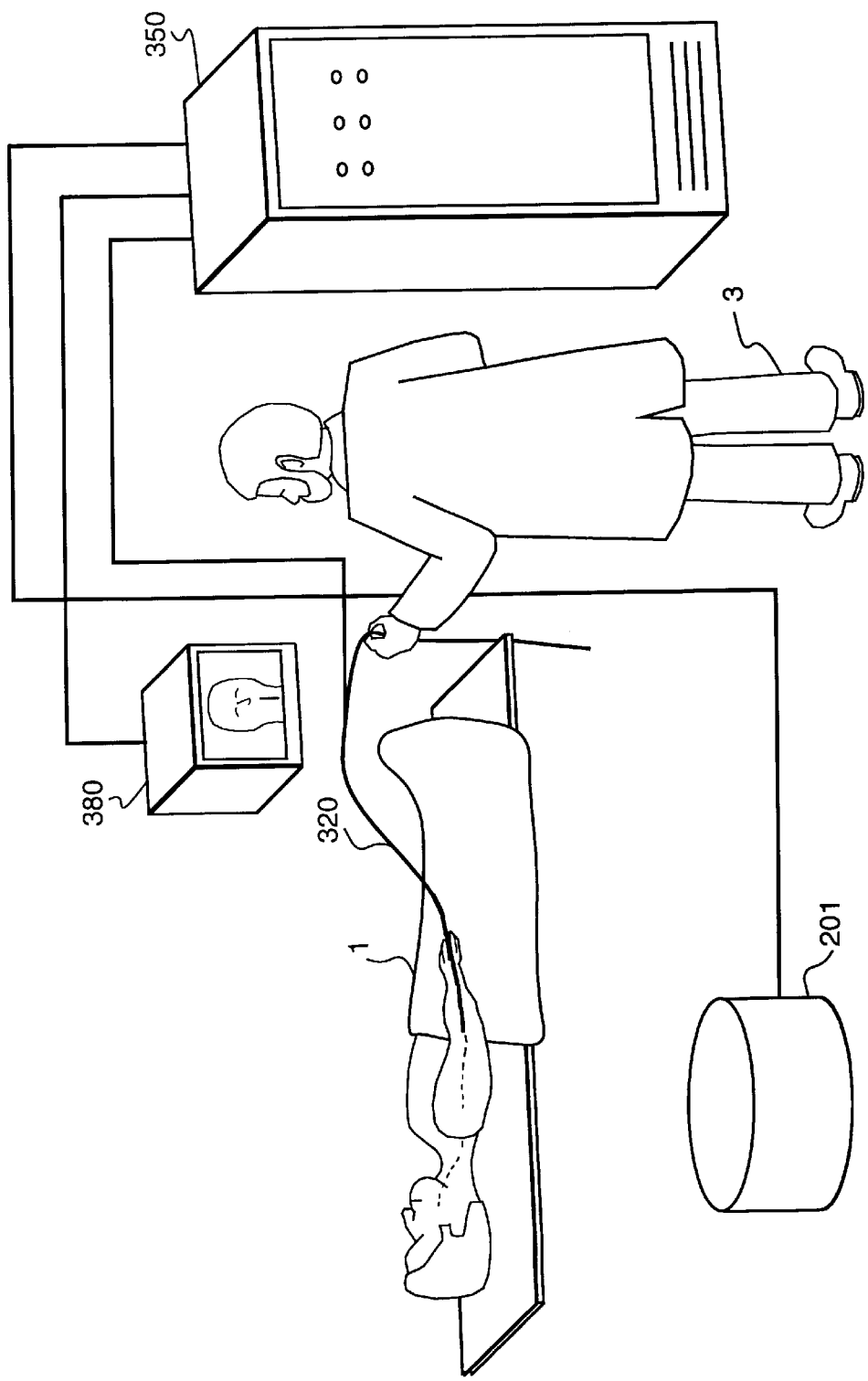
FIG. 2 is a simplified block diagram of the present invention employing an RF tracking system used to follow an invasive device in real-time.

Systems for creating a tissue map according to the present invention are shown in FIGS. 1, and 2. These track the real-time location of an invasive device 320, such as a catheter, within a subject 1.

An operator 3, typically a Physician, inserts invasive device 320 into a lumen of subject 1. Invasive device 320 has an element which is tracked by a tracking means. For magnetic resonance (MR) tracking, the tracked element may be an MR coil, or a plurality of MR coils. These coils may be either receive or transmit coils. The tracked element may also be a quantity of a material which is imaged well in an MR image, such as Gadolinium chelate solution.

The tracking means for MR tracking includes a magnet assembly 101 having RF and gradient coils, and system electronics 340. An MR signal is acquired in magnet assembly 101 and passed to system electronics 340 which interpret the signal into a location, or plurality of locations which are tracked in real-time, or near real-time, and displayed on a monitor 380.

In RF tracking, as shown in FIG. 2, the tracked element may be an RF coil, or a plurality of RF coils attached to the invasive device 320. An external coil 201 operates to transmit an RF signal which is received by the RF coils attached to the invasive device 320.

RF tracking system electronics 350 interpret the signals to determine the location and orientation of invasive device 320 in real-time, and display the location on a monitor 380.

In an alternative embodiment, external coil 201 may be a receive coil and the RF coils attached to invasive device 320 may be transmit coils.

Figure 3:
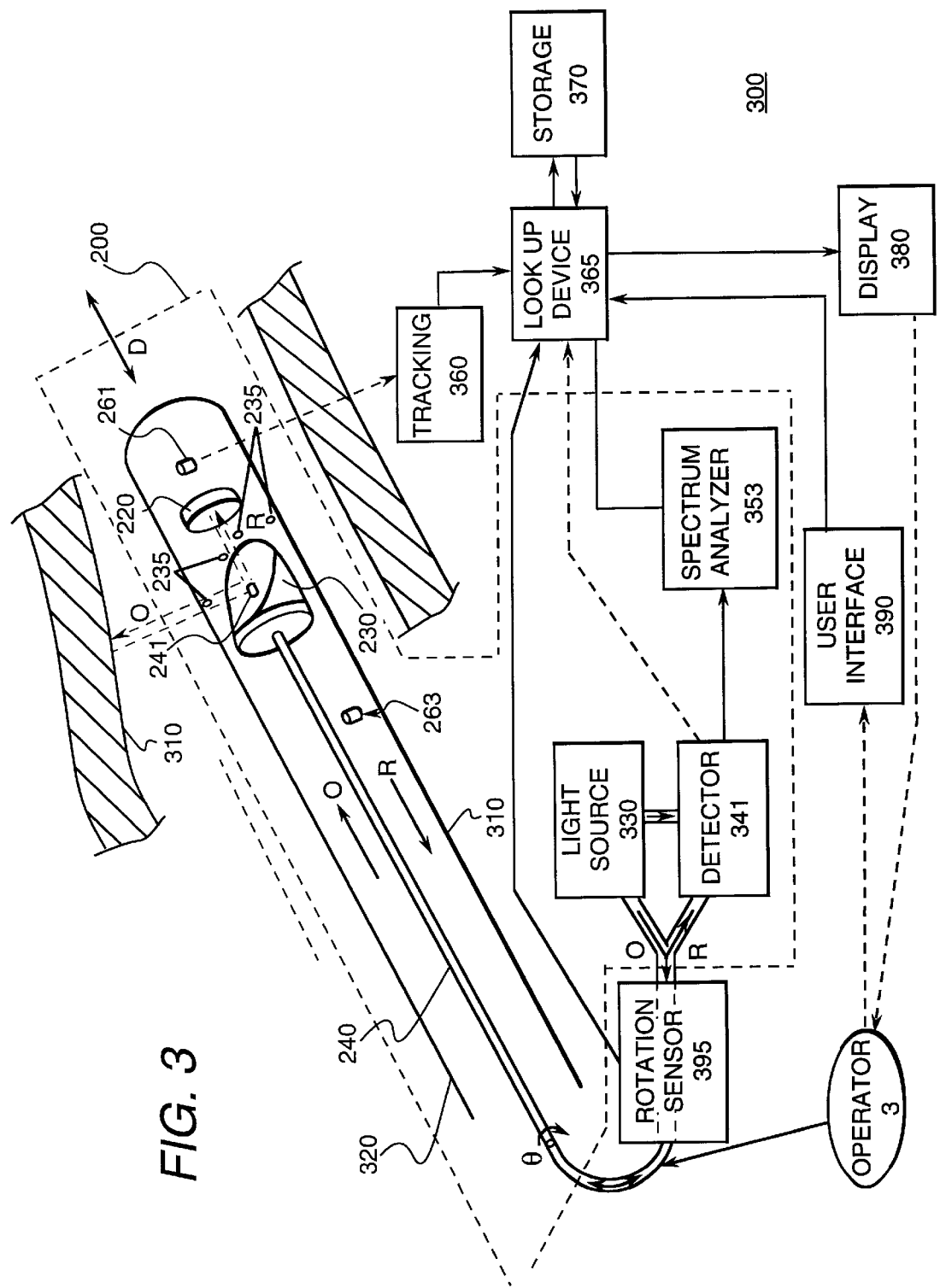
FIG. 3 is a schematic representation of a system according to the present invention for the acquisition of a visible spectrum luminal map indicating health of luminal tissue.

In FIG. 3, a system for tissue mapping 300 is shown. Tissue mapping system 300 includes an optical spectrum acquisition device 200 which is intended for the spectral analysis of tissue. An invasive device 320 is shown in a lumen 310 of subject 1. Lumen 310 may be a vessel, intestine, esophagus, stomach, or other opening within the subject to be imaged. This may also include cavities such as the abdominal cavity which are only accessible through an incision.

Invasive device 320, inserted in lumen 310, is tracked by a device tracking means 360 which may be magnetic resonance (MR) tracking, or radio frequency (RF) tracking.

Invasive device 320 may be moved further in, or retracted out of luminal cavity 310, and therefore its displacement D along the luminal cavity can be measured.

A fiber optic cable 240 connects a white light source 330 to an exit port 241. A white light outgoing beam O is passed down fiber optic cable 240, exits at exit port 241, and impinges upon a fixed parabolic mirror 220.

Outgoing beam O is then reflected back to a rotating planar mirror 230. Rotating planar mirror 230 reflects outgoing beam O to impinge on lumen wall 310.

Lumen wall 310 absorbs portions and reflects portions of the white light beam being the return beam R, with its spectrum indicating morphology of lumen wall at the impingement point.

Return beam R is reflected off of rotating planar mirror 230 and fixed mirror 220 and back into port 241. From port 241 it is passed back down fiber optic cable 240.

Return beam R is then passes to a detector 341 which converts the reflected light into an electronic signal which is passed to a spectrum analyzer 353.

Spectrum analyzer 353 determines the spectral content of the electronic signal representing the reflected light spectrum.

A look up device 365 receives the spectral information from spectrum analyzer 353 and correlates this with known, stored, morphological information. For example, if the lumen is a vessel wall and the reflected signal has an amplitude which is high in the yellow frequency band, this may indicate plaque buildup on the inside of the artery. Spectral signals with a high amplitude in the red frequencies may indicate hemorrhaging.

A first device locating means 261 and a second locating means 263 are tracked by conventional MR tracking or RF tracking to determine translational displacement D of invasive device 320. The translational displacement D from tracking device 360 is provided to look up device 365.

Two device locating means are shown 261, 263, however, only one is required to determine the location of invasive device 320. By using two device locating means, the orientation of invasive device 320 may also be determined.

A rotation sensor 395 determines the angular rotation θ of fiber optic cable 240, and therefore the angular displacement θ of rotating mirror 230 and the optical beam. Angular rotation θ from rotation sensor 395 is also provided to look up device 365

The morphology information is then associated with the translational displacement D and angular displacement θ of the optical beam in a look up device 365 to create a morphology map in three dimensions. The 3D morphological map may then be stored in a storage device 370 for later retrieval.

Operator 3 may interact with a user interface 390 to request images of portions of lumen 310. Operator 3 may also specify how to view lumen 310, and set the viewpoint from which it is to be viewed.

Images may be color coded to distinguish between different tissue morphology. Look up device 365 receives the user defined input and provides images on a display 380 to operator 3.

Operator 3 may manually rotate or move invasive device 320 to acquire information and images of different portions of lumen 310.

In an alternative embodiment, a detector 341 is a conventional interferometer which receives the reflected light beam R.

If it is desired to measure distance between rotating mirror 230 and the lumen wall 310, light source 330 should have a monochromatic output and detector 341 should be an interferometer. Instantaneous distances can then be determined. The measured distances would be provided to look up device 365, and stored with the other information in storage device 370. This would provide radii and diameters at different locations in subject 1. This would allow look up device 365 to create 3D maps of the lumen. These maps may be used alone, or to supplement the morphology maps.

Another alternative embodiment would pass a clear fluid through the inside of invasive device 320 when the optical beams are operating and the system is acquiring data. The fluid would squirt through a plurality of ports 235 in invasive device 320 to facilitate transmission of the outgoing and reflected beams when the lumen is full of a fluid which attenuates or scatters light. For example, if invasive device 320 was inserted into a vessel of subject 1, sterile saline solution could be squirted through ports 235 to temporarily displace blood in a local region allowing transmission of the optical beam. This would greatly facilitate beam transmission and produce more accurate morphology maps.

The present invention may be employed for a number of different diagnostic procedures. For example, invasive device 320 may be used to determine the biochemical makeup of a blood vessel wall within a living patient. Other embodiments of the present invention could be used to diagnose abnormal tissue in the walls of other body structures such as the colon, small intestines, stomach or esophagus. It should be noted, however, that the present invention could also be employed in non-medical application if desired.

The present invention can also employ ultra-violet, visible, or infra-red light.

In still another embodiment, fluorescent tracers which accumulate in specific types of tissue may be used. The present invention can then easily accurately map the tissue by monitoring the fluorescence.

Conventional spectroscopy methods, such as Raman Spectroscopy, may be employed with the present invention.

While several presently preferred embodiments of the novel invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A system for creating a tissue map of a lumen within a subject comprising:
    a) an invasive device for insertion into a subject;
    b) an optical spectrum acquisition device in an insertion end of the invasive device, disposed to project a light beam to irradiate the lumen at an angular displacement θ around the insertion end of the invasive device, and to receive reflected light, the optical spectrum acquisition device being adapted to create a signal representing the light spectrum reflected from the lumen, and the optical spectrum acquisition device being adapted to measure a respective diameter of the lumen at a respective location of the invasive device within the lumen;
    c) at least one device locating means attached to the insertion end of the invasive device;
    d) a tracking means for tracking locations of the device locating means within the subject;
    e) a rotation sensor for measuring the angular displacement θ of the irradiating beam;
    f) a storage device capable of storing an indication of tissue type and corresponding 3D locations for later retrieval;
    g) a display;
    h) a look up device coupled to each of the following: the optical spectrum acquisition device, the storage device, the display, the tracking means and the rotation sensor, the look up device being configured to convert the tracked location from the tracking means in correspondence with the angular displacement of the irradiating beam and the respective diameter, to estimate a 3D location of the lumen reflecting the irradiating beam, said look up device to correlate the reflected light spectrum to a color frequency stored in the look up device indicating a tissue type, to store the tissue type along with the 3D location represented in the storage device, and to display the 3D locations and corresponding tissue type as a tissue map on the display.

2. The system for creating a tissue map of lumen of claim 1 further comprising:
    an interferometer device operating to receive the reflected light, to accurately determine a distance D from the lumen to the optical spectrum acquisition device, and provides it to look up device to more accurately determine the 3D location on the lumen reflecting the irradiating beam, resulting in tissue maps incorporating actual measured lumen diameters.

3. The system for creating a tissue map of lumen of claim 1 wherein the an optical spectrum acquisition device comprises:
    a) a fiber optic cable running through the invasive device having an optical port at one end and the other end being an equipment end;
    b) a light source coupled to the equipment end of the fiber optic cable operating to create an outgoing light beam O and pass it through the fiber optic cable and out the optical port;
    c) an angled rotating mirror attached to the optical port end of the fiber optic cable, having a mirror angled with respect to an axis though the light beam, and capable of rotating substantially about this axis upon rotation of the fiber optic cable, operating to reflect the outgoing beam O to the lumen and the reflected beam R from said lumen back in the opposite direction;
    d) a planar mirror for reflecting the outgoing light beam O from the optical port back toward the rotating mirror causing it to reflect laterally to impinge upon said lumen, and for reflecting the return beam back R into the optical port;
    e) a detector coupled to the equipment end of optical cable, for converting the reflected beam R into an electronic signal; and
    f) a spectrum analyzer coupled to the detector and the look up device, operating to extract spectral information from the electronic signal from detector, and provide it to look up device for tissue determination.

4. The system for creating a tissue map of lumen of claim 1 further comprising:
    a user interface for interacting with an operator to acquire operator define input and operating to provide this input to the lookup device.

5. A system for indicating tissue type of a lumen within a subject comprising:
- a) an invasive device for insertion into a subject;
- b) means for projecting a light beam to irradiate the lumen and to receive reflected light from the lumen, the projecting means being adapted to create a signal representing the light spectrum from the lumen and the projecting means further being adapted to measure a respective diameter of the lumen at a location within the lumen;
- c) a tracking means for tracking locations of the invasive device; and,
- d) means for receiving the reflected light spectrum, respective diameter measurements, and tracked locations and correlating the reflected light spectrum to a color frequency indicative of tissue type characteristic stored in the receiving and correlating means to indicate the tissue type of the lumen at said tracked locations.

6. The system for indicating tissue type of a lumen of claim 5 wherein the projecting means is configured to project a light beam to irradiate the lumen at an angular displacement $\theta$ around an insertion end of the invasive device.

7. The system for indicating tissue type of a lumen of claim 6 further comprising:
- a) the invasive device being movable within the subject by an operator; and,
- b) at least one device locating means attached to invasive device;
- c) the receiving and correlating means being coupled to the tracking means and adapted to indicate the tissue type of the lumen according to operator movement of the invasive device.

8. The system for indicating tissue type of a lumen of claim 7 further comprising a display and means for displaying indicated tissue type on the display.

* * * * *